(12) United States Patent
Jiao et al.

(10) Patent No.: US 10,870,612 B1
(45) Date of Patent: Dec. 22, 2020

(54) METHOD FOR SIMULTANEOUSLY EXTRACTING LYCOPENE AND CITRULLINE FROM WATERMELON

(71) Applicant: ZHENGZHOU FRUIT RESEARCH INSTITUTE CHINESE ACADEMY OF AGRICULTURAL SCIENCES, Zhengzhou (CN)

(72) Inventors: Zhonggao Jiao, Zhengzhou (CN); Jiechao Liu, Zhengzhou (CN); Chunling Zhang, Zhengzhou (CN); Qiang Zhang, Zhengzhou (CN); Hui Liu, Zhengzhou (CN); Zhenzhen Lv, Zhengzhou (CN); Wenbo Yang, Zhengzhou (CN); Dalei Chen, Zhengzhou (CN)

(73) Assignee: ZHENGZHOU FRUIT RESEARCH INSTITUTE CHINESE ACADEMY OF AGRICULTURAL SCIENCES, Zhengzhou (CN)

( * ) Notice: Subject to any disclaimer, the term of this patent is extended or adjusted under 35 U.S.C. 154(b) by 0 days.

(21) Appl. No.: 16/888,782

(22) Filed: May 31, 2020

Related U.S. Application Data

(63) Continuation of application No. PCT/CN2019/076477, filed on Feb. 28, 2019.

(51) Int. Cl.
*C07C 7/00* (2006.01)
*C07C 273/18* (2006.01)

(52) U.S. Cl.
CPC .......... *C07C 7/005* (2013.01); *C07C 273/189* (2013.01)

(58) Field of Classification Search
CPC ........................... C07C 7/005; C07C 273/189
See application file for complete search history.

(56) References Cited

FOREIGN PATENT DOCUMENTS

| CN | 1611467 A | 5/2005 |
|---|---|---|
| CN | 101880245 A | 11/2010 |
| CN | 103360283 A | 10/2013 |

*Primary Examiner* — Thuan D Dang
(74) *Attorney, Agent, or Firm* — SZDC Law P.C.

(57) ABSTRACT

A method for simultaneously extracting Lycopene and Citrulline from a watermelon includes: separating the rind and the pulp of the watermelon, preprocessing the rind, and using the preprocessed rind to extract the Citrulline; subjecting the pulp to biological enzymolysis and filtering, centrifuging a filtrate, using a precipitate and a filter residue obtained after the centrifuging to extract the Lycopene, and using a supernatant obtained after the centrifuging to extract the Citrulline. By using the method for synchronously extracting Lycopene and Citrulline from the watermelon of the present invention, about 0.5 kg of Lycopene (6% content) and more than 1.2 kg of Citrulline which are worthy of nearly ten thousand yuan can be extracted from each ton of imperfect watermelons, the economic benefit of each ton of watermelons can be increased by more than 5000 yuan after extraction costs are deducted, and the method is high in economic benefits.

9 Claims, No Drawings

METHOD FOR SIMULTANEOUSLY EXTRACTING LYCOPENE AND CITRULLINE FROM WATERMELON

This application is Bypass Continuation Application of PCT/CN2019/076477, filed on Feb. 28, 2019, which claims priority to Chinese Patent Application No.: CN 201811002394.9, filed on Aug. 30, 2018, which is incorporated by reference for all purposes as if fully set forth herein.

BACKGROUND OF THE INVENTION

1. Technical Field

The invention belongs to the technical field of natural substance extraction, and particularly relates to a method for synchronously extracting Lycopene and Citrulline from watermelon.

2. Description of Related Art

Watermelons are widely planted in China, with short growth cycles and high yields. The annual planting area is about 2 million hectares, with a total output of 68 million tons, accounting for 58.99% and 71.45% of the world's total watermelon cultivation area and total output respectively, and both ranking first in the world. Due to the strong seasonality of watermelon planting, the market is concentrated, and it is not easy to store. The imbalance between supply and demand has caused watermelon prices to fall sharply or even to overstock, causing a lot of decay. In addition, the defective melons in the planting process are not suitable for fresh sales, and often can only be rotten in the ground or sold extremely cheaply, resulting in a waste of resources. The key to solving these problems lies in vigorously developing deep processing of watermelon and increasing the added value of watermelon.

In addition to fat and cholesterol, watermelon contains a large amount of glucose, malic acid, fructose, amino acids, Lycopene and rich vitamin C and other substances. It is a nutrient-rich, pure, and safe food.

At present, there are extraction methods for functional components such as Citrulline and Lycopene in watermelon. However, these functional components exist in different parts of watermelon. Extracting a certain natural substance singly can not maximize the making full use of the nutritional value of watermelons. It has caused waste of resources and increased production costs.

BRIEF SUMMARY OF THE INVENTION

In view of the problems existing in the prior art, the object of the present invention is to provide a method for synchronously extracting Lycopene and Citrulline from watermelon, which maximize the making full use of the nutritional value of watermelon, reduce production costs and obtain higher economic benefits.

The technical solution adopted by the invention to fulfill the above objective is as follows:

A method for synchronously extracting Lycopene and Citrulline from watermelon:

separate the rind and pulp of watermelon; the Citrulline is extracted from the rind after pretreatment; process the pulp with biological enzymolysis, then filter to obtain filter residue and filtrate; the filtrate is centrifuged to obtain precipitate and supernatant, the precipitate is mixed with the filter residue above to use to extract Lycopene, and the supernatant is used to extract Citrulline.

Wherein the process of biological enzymolysis, the amount of biological enzyme added is 0.1-0.3% (m/m), with the temperature maintaining at 40-50° C., and then performing 1-2 hours of enzymolysis.

The biological enzyme is at least one of pectinase, cellulase, and protease.

In one embodiment, the biological enzymatic treatment of the pulp is:

Watermelon pulp is beaten after the seeds are removed. The slurry is added with 0.3% (m/m) of biological enzymes to perform enzymatic hydrolysis for 1.5 h at 45° C. Then the enzymatic slurry is filtered to obtain filter residue and filtrate, and the filtrate is centrifuged to collect the precipitate. After being lyophilized, the precipitate and filter residue which were combined are ground into powder for extraction of Lycopene; the supernatant after centrifugation is used for extraction of Citrulline.

The method for extracting Lycopene is:

(1) Ultrasound-assisted organic solvent leaching: add ethyl acetate to the powder ground from the filter residue and the precipitate at a ratio of 1:4-1:8 (kg/L) and mix evenly with the temperature 40-50° C., ultrasonic output power 80-120 W, extraction time 30-90 min, and extraction times twice to obtain liquid of crude Lycopene extract;

(2) Concentrated under reduced pressure: the liquid of crude Lycopene extract is concentrated under reduced pressure at 40° C., and the solvent is recovered to obtain a crude Lycopene;

(3) Purification: Anhydrous ethanol is added to the crude Lycopene at a material-liquid ratio of 1:3 (kg/L) to embathe for twice. And then a Lycopene powder is obtained after removing the anhydrous ethanol.

In one embodiment, the pretreatment of the watermelon rind is:

Remove the outer skin of watermelon rind, and then squeeze the rind to obtain the filter residue and rind juice. The filter residue is subjected to ultrasound-enzyme assisted solvent leaching to obtain an extract solution. And then the extract solution is mixed with the rind juice and the supernatant which is obtained by centrifuging the pulp to obtain a pretreatment material for extracting Citrulline.

In one embodiment, the pretreatment of the watermelon rind is:

Remove the outer skin of watermelon rind, and ground the rind into powder after being dried. The powder is subjected to ultrasound-enzyme assisted solvent leaching and filtered to obtain a primary extraction solution. The filter residue is subjected to ultrasound-enzyme assisted solvent leaching, and then filtered to obtain a secondary extraction solution. The secondary extraction solution is mixed with the primary extraction solution and the supernatant after centrifugation of pulps, to obtain a pretreatment material for extracting Citrulline.

In any of the preceding embodiments, the ultrasound-enzyme assisted solvent leaching is:

Water is added to the pretreated material at a material-liquid ratio of 1:10-1:20 (kg/L), and then 0.1% (m/m) of pectinase and 0.1% (m/m) of cellulose are also added to the above pretreated material. Adjust pH to 4.0, ultrasonic power to 100-140 W, extraction temperature to 30-50° C., extraction time to 60-120 min, and extraction times to twice.

In one embodiment, the extraction method of Citrulline is:

(1) Microbial fermentation: 5% (v/v) yeast is added to the pretreated material to ferment for 24 hours to remove sugar.

(2) Ion-exchange resin purification: the pretreated material after microbial fermentation is filtered to remove yeasts, and added to HD-8 activated wet resin to adsorb Citrulline, and then eluted with 0.5 mol/L ammonia solution for 2 BV/h of the elution rate to obtain Citrulline eluent.

(3) Macroporous adsorption resin discoloration: mix XAD-761 activated wet resin with Citrulline eluent at 1:20 (g/mL), and perform static adsorption on condition of 100-150 r/min for 2 h at room temperature.

(4) Crystallization and recrystallization:
a. The crude Citrulline extract is concentrated under vacuum to a soluble solid content ≥30%, the pH of the concentrated solution is adjusted to 5.97, and the Citrulline crystals are precipitated at 4° C. The precipitate is centrifuged, washed, and dried to obtain a white powdered solid of Citrulline crystals.
b. Dissolve the Citrulline powder of step (a) with water, adjust the pH to 5.97, add 0.1% (m/m) Citrulline crystals as seed crystals, precipitate the Citrulline crystals at 4° C., and centrifuge to separate the precipitates.
c. Repeat step (b) 1-2 times, centrifuge the precipitate, wash, and dry to obtain a refined solid powder of Citrulline.

The Lycopene and/or Citrulline which be prepared by the method described above.

The Lycopene prepared by the above method can apply to the preparation of foods for anti-oxidation, anti-aging, anti-hypoxia response, prevention and treatment of cancer, and protection of cardiovascular.

The Citrulline prepared by the above method can apply to the preparation of foods for enhancing immunity, anti-oxidation, improving exercise function, protecting cardiovascular and cerebrovascular, and improving male sexual function.

Based on the above scheme, the food is a health product.

The strain number of yeast is CICC-1012, China Center of Industrial Culture Collection.

The pectinase, cellulase, and protease were purchased from Tianjin Lihua Enzyme Preparation Technology Co., Ltd., and the enzyme activity was 1000 U/mg.

Advantages of the technical solution of the present invention:

The synchronous extraction method of watermelon Lycopene and Citrulline achieves sufficient and efficient utilization of watermelon resources. The extraction rate of Lycopene and Citrulline is high, and the purity of the extracted Citrulline is high. The extracted Lycopene and Citrulline meet the relevant sanitary requirements and product quality standards, and can be used as raw materials in the food and health products industry, and has natural advantages of safety.

The present invention uses a combination of ultrasonic, enzymatic and other auxiliary extraction methods to ensure efficient extraction under low temperature conditions. The conditions are mild and the operation is simple and safe.

Using the synchronous extraction method of watermelon Lycopene and Citrulline of the present invention, about 0.5 kg (6% content) of Lycopene and more than 1.2 kg of Citrulline can be extracted per ton of inferior watermelon, with a value of nearly 10,000 yuan. After deducting the cost of extraction, each ton of watermelon can still increase the economic benefit by more than 5,000 yuan, which has higher economic benefits.

DETAILED DESCRIPTION OF THE INVENTION

Terms used in the present invention have the meanings generally understood by those of ordinary skill in the art unless otherwise specified.

The present invention will be described in further detail with reference to specific embodiments and with reference to data. The following examples are only for the purpose of illustrating the present invention, and are not intended to limit the scope of the present invention in any way.

Embodiment 1

A method for synchronously extracting Lycopene and Citrulline from watermelon, the steps are as follows:
Isolated the rind and pulp of watermelon;
Treatment of pulp:
Watermelon pulp was beaten after the seeds were removed. The slurry was added with 0.1% pectinase, 0.1% cellulase, and 0.1% protease to perform enzymatic hydrolysis for 1.5 h at 45° C. Then the enzymatic slurry was filtered to obtain filter residue and filtrate; the filtrate is centrifuged (4000 r/min, room temperature, 10-20 min) to obtain precipitate and supernatant. After being lyophilized, the precipitate and filter residue which have been already combined were ground into powder for extraction of Lycopene; the supernatant after centrifugation would be used for extraction of Citrulline.

The extraction method of Lycopene is:
(1) Ultrasound-assisted organic solvent leaching: added ethyl acetate to the powder ground from the filter residue and the precipitate at a ratio of 1:6 (kg/L) and mixed evenly with the temperature 45° C., ultrasonic output power 100 W, extraction time 30 min, and extraction times twice to obtain liquid of crude Lycopene extract;
(2) Concentrated under reduced pressure: the liquid of crude Lycopene extract was concentrated under reduced pressure at 40° C., and the solvent was recovered to obtain a crude Lycopenet;
(3) Purification: Anhydrous ethanol was added to the crude Lycopene at a material-liquid ratio of 1:3 (kg/L) to embathe for twice. And then a Lycopene powder was obtained after removing the anhydrous ethanol.

Treatment of watermelon rind:
Remove the outer skin of watermelon rind, and then squeeze the rind to obtain the filter residue and rind juice.

Water was added to the filter residue at a material-liquid ratio of 1:10 (kg/L), and then 0.1% (m/m) of pectinase and 0.1% (m/m) of cellulose were also added to the above filter residue. Adjusted pH to 4.0, ultrasonic power to 100 W, extraction temperature to 50° C., extraction time to 90 min, and extraction times to twice. And then the combined extract was obtained.

The above combined extract was mixed with the supernatant which was obtained by centrifugation of the rind juice and pulp to obtain a pretreatment material for extracting Citrulline.

Extraction method of Citrulline:
(1) Microbial fermentation: 5% (v/v) yeast was added to the pretreated material to ferment for 24 hours to remove sugar.
(2) Ion-exchange resin purification: the pretreated material after microbial fermentation was filtered to remove yeasts, and added to HD-8 activated wet resin to perform the dynamic exchange adsorption of Citrulline, and then eluted with 0.5 mol/L ammonia solution for 2 BV/h of the elution rate.

The dynamic exchange adsorption is that 180 g of activated wet resin was packed in a glass chromatography column with an inner diameter of 26 mm and a height of 400 mm, and the Citrulline extract solution after fermentation by microorganisms was passed through the resin column at a speed of 2 BV/h to adsorb Citrulline.

(3) Macroporous adsorption resin discoloration: mixed XAD-761 activated wet resin with Citrulline eluent at 1:20 (g/mL), and performed static adsorption on condition of 100-150 r/min for 2 h at room temperature.

(4) Crystallization and recrystallization:

a. The crude Citrulline extract was concentrated under vacuum to a soluble solid content of ≥30%, the pH of the concentrated solution was adjusted to 5.97, and the Citrulline crystals were precipitated at 4° C. The precipitate was centrifuged, washed, and dried to obtain a white powdered solid of Citrulline crystals.

b. Dissolved the Citrulline powder of step (a) with water, adjusted the pH to 5.97, added 0.1% Citrulline crystals as seed crystals, precipitated the Citrulline crystals at 4° C., and centrifuged to separate the precipitates.

c. Repeated step (b) 1-2 times, centrifuged the precipitate, washed, and dried to obtain a refined solid powder of Citrulline.

After testing, the extraction rate of Lycopene was 91.57%; the extraction rate of Citrulline was 93.43%, and the purity of Citrulline was 99.35%.

Embodiment 2

A method for synchronously extracting Lycopene and Citrulline from watermelon, the steps are as follows:

Isolated the rind and pulp of watermelon;

Treatment of pulp:

Watermelon pulp was beaten after the seeds were removed. The slurry was added with 0.1% pectinase, 0.1% cellulase, and 0.1% protease to perform enzymatic hydrolysis for 1.5 h at 45° C. Then the enzymatic slurry was filtered to obtain filter residue and filtrate; the filtrate is centrifuged (4000 r/min, room temperature, 10-20 min) to obtain precipitate and supernatant. After being lyophilized, the precipitate and filter residue which have been already combined were ground into powder for extraction of Lycopene; the supernatant after centrifugation would be used for extraction of Citrulline.

The extraction method of Lycopene is:

(1) Ultrasound-assisted organic solvent leaching: added ethyl acetate to the powder ground from the filter residue and the precipitate at a ratio of 1:6 (kg/L) and mixed evenly with the temperature 45° C., ultrasonic output power 100 W, extraction time 30 min, and extraction times twice to obtain liquid of crude Lycopene extract;

(2) Concentrated under reduced pressure: the liquid of crude Lycopene extract was concentrated under reduced pressure at 40° C., and the solvent was recovered to obtain a crude Lycopenet;

(3) Purification: Anhydrous ethanol was added to the crude Lycopene at a material-liquid ratio of 1:3 (kg/L) to embathe for twice. And then a Lycopene powder was obtained after removing the anhydrous ethanol.

Treatment of watermelon rind:

The watermelon rind which the outer skin was removed was ground into powder after being dried;

Water was added to the powder at a material-liquid ratio of 1:10 (kg/L), then 0.1% (m/m) of pectinase and 0.1% (m/m) of cellulose were also added to the above powder. Adjusted pH to 4.0, ultrasonic power to 100 W, extraction temperature to 50° C., and extraction time to 90 min, and a primary extraction solution was obtained after being filtered. Water was added to the filter residue at a material-liquid ratio of 1:10 (kg/L), then 0.1% (m/m) of pectinase and 0.1% (m/m) of cellulose were also added to the above filter residue. Adjusted pH to 4.0, ultrasonic power to 100 W, extraction temperature to 50° C., and extraction time to 90 min, and a secondary extraction solution was obtained after being filtered.

The secondary extraction solution was mixed with the primary extraction solution and the supernatant after centrifugation of pulp to obtain a pretreatment material for extracting Citrulline.

Extraction method of Citrulline:

(1) Microbial fermentation: 5% (v/v) yeast was added to the pretreated material to ferment for 24 hours to remove sugar.

(2) Ion-exchange resin purification: the pretreated material after microbial fermentation was filtered to remove yeasts, and added to HD-8 activated wet resin to perform the dynamic exchange adsorption of Citrulline, and then eluted with 0.5 mol/L ammonia solution for 2 BV/h of the elution rate.

The dynamic exchange adsorption is that 180 g of activated wet resin was packed in a glass chromatography column with an inner diameter of 26 mm and a height of 400 mm, and the Citrulline extract solution after fermentation by microorganisms was passed through the resin column at a speed of 2 BV/h to adsorb Citrulline.

(3) Macroporous adsorption resin discoloration: mixed XAD-761 activated wet resin with Citrulline eluent at 1:20 (g/mL), and performed static adsorption on condition of 100-150 r/min for 2 h at room temperature.

(4) Crystallization and recrystallization:

a. The crude Citrulline extract was concentrated under vacuum to a soluble solid content of ≥30%, the pH of the concentrated solution was adjusted to 5.97, and the Citrulline crystals were precipitated at 4° C. The precipitate was centrifuged, washed, and dried to obtain a white powdered solid of Citrulline crystals.

b. Dissolved the Citrulline powder of step (a) with water, adjusted the pH to 5.97, add 0.1% Citrulline crystals as seed crystals, precipitated the Citrulline crystals at 4° C., and centrifuged to separate the precipitates.

c. Repeat step (b) 1-2 times, centrifuged the precipitate, washed, and dried to obtain a refined solid powder of Citrulline.

After testing, the extraction rate of Lycopene was 91.76%; the extraction rate of Citrulline was 92.98%, and the purity of Citrulline was 98.77%.

1. Analysis and test results of Lycopene and Citrulline extract of the present invention (1) Analysis of Lycopene The hygienic indicators such as heavy metals and microorganisms in the watermelon Lycopene extract extracted in Example 1 were tested and compared with the quality standards of commercially available Lycopene oleoresin products. The results are shown in Table 1.

TABLE 1

| Hygienic indicators of watermelon Lycopene extract | | | |
| --- | --- | --- | --- |
| Test item | Unit | Test result | Commercial product standard |
| Arsenic | mg/kg | $5.3 \times 10^{-2}$ | ≤5 |
| Lead | mg/kg | Not detected | ≤10 |
| Total bacteria | CFU/g | <10 | ≤1000 |
| Yeast and mold | CFU/g | <10 | ≤100 |
| E.coli | MPN/100 g | <30 | ≤40 |

From the test results in Table 1, it can be known that the indexes of heavy metals and microorganisms of the watermelon Lycopene extract extracted by the method of the present invention meet the relevant sanitary requirements and product quality standards.

(2) Analysis of Citrulline

The physicochemical and hygienic indicators of the Citrulline extract extracted in Example 1 were analyzed and compared with the quality standards of commercially available Citrulline products. The results are shown in Table 2.

TABLE 2

Physicochemical and hygienic indicators of Citrulline extract

| Test item | Unit | Test result | Commercial product standard |
|---|---|---|---|
| Citrulline content | % | 92.48 | — |
| Ammonium content (NH$_4$) | % | <0.02 | ≤0.02 |
| Chloride | % | <0.02 | ≤0.02 |
| Slsfate (SO$_4$) | % | <0.02 | ≤0.02 |
| Iron | mg/kg | <10 | ≤10 |
| Arsenic | mg/kg | $2.7 \times 10^{-2}$ | ≤1 |
| Lead | mg/kg | Not detected | ≤10 |

From the test results in Table 2, it can be known that the heavy metal and microbe indexes of the Citrulline extract extracted by the method of the present invention meet the relevant health requirements and product quality standards.

Economic Benefits

The current price of Lycopene on the Chinese market is about 2,000 yuan/kg (6% content), and Citrulline extracted from plants can be sold for about $1,000/kg in the United States. By using the method of the present invention, about 0.5 kg (6% content) of Lycopene and more than 1.2 kg of Citrulline can be extracted per ton of inferior watermelon, and the value is nearly 10,000 yuan. After deducting the extraction cost, the economic benefit can still increase by more than 5000 yuan per ton of watermelon. Based on the annual output of 70 million tons of watermelon in China, if 10% of the processing capacity can be achieved, the output value can reach more than 60 billion yuan. If the watermelon with higher content of Lycopene and Citrulline is used as the raw material, the extraction yield and economic benefits will be higher.

The above embodiments are only used to illustrate the technical solutions of the present invention, but not to limit them. Although the present invention has been described in detail with reference to the foregoing embodiments, the technical solutions described in the embodiments are still possibly modified, or some of the technical features are equivalently replaced by those skilled in the art by referring to the foregoing. These modifications or replacements do not depart from the spirit and scope of the technical solutions claimed in the present invention.

What is claimed is:

1. A method for simultaneously extracting Lycopene and Citrulline from a watermelon, comprising:
    separating a rind and a pulp of the watermelon;
    extracting Citrulline from the rind after a pretreatment of the rind;
    processing the pulp with a biological enzymolysis, then filtering to obtain a filter residue and a filtrate;
    centrifuging the filtrate to obtain a precipitate and a supernatant,
    wherein the precipitate is mixed with the filter residue to be used to extract Lycopene, and the supernatant is used to extract Citrulline.

2. The method for simultaneously extracting Lycopene and Citrulline from the watermelon according to claim 1, wherein the biological enzymolysis comprises: adding a biological enzyme in an amount of 0.1-0.3% (m/m), with a temperature maintaining at 40-50° C., and then performing an enzymolysis for 1-2 hours.

3. The method for simultaneously extracting Lycopene and Citrulline from the watermelon according to claim 2, wherein the biological enzyme is at least one selected from the group consisting of pectinase, cellulase and protease.

4. The method for simultaneously extracting Lycopene and Citrulline from the watermelon according to claim 1, wherein the biological enzymolysis comprises:
    beating the pulp to form a slurry after seeds are removed;
    adding 0.3% (m/m) of biological enzymes to the slurry to perform an enzymatic hydrolysis for 1.5 h at 45° C.;
    filtering the slurry to obtain the filter residue and the filtrate, and centrifuging the filtrate to collect the precipitate; after being lyophilized, combining the precipitate and filter residue and grounding into powder for extraction of Lycopene; and using the supernatant after centrifugation for extraction of Citrulline.

5. The method for simultaneously extracting Lycopene and Citrulline from the watermelon according to claim 4, wherein the extraction of Lycopene comprises:
    (1) ultrasound-assisted organic solvent leaching: adding ethyl acetate to the powder grounded from the filter residue and the precipitate at a ratio of 1:4-1:8 (kg/L) and mixing evenly at a temperature of 40-50° C., an ultrasonic output power of 80-120 W, an extraction time of 30-90 min, and extracting twice to obtain of a crude Lycopene extract solution;
    (2) concentrated under reduced pressure: concentrating the crude Lycopene extract solution under reduced pressure at 40° C. to obtain a crude Lycopene;
    (3) purification: Anhydrous adding anhydrous ethanol to the crude Lycopene at a material-liquid ratio of 1:3 (kg/L) to embathe for twice; and then removing the anhydrous ethanol to obtain a Lycopene powder.

6. The method for simultaneously extracting Lycopene and Citrulline from the watermelon according to claim 1, wherein the pretreatment of the rind comprises:
    removing an outer skin of the rind, and then squeezing the rind to obtain the filter residue and the filtrate; subjecting the filter residue to an ultrasound-enzyme assisted solvent leaching to obtain an extract solution; and then mixing the extract solution with the filtrate and a pulp supernatant which is obtained by centrifuging the pulp to obtain a pretreatment material for extracting Citrulline.

7. The method for simultaneously extracting Lycopene and Citrulline from the watermelon according to claim 1, wherein the pretreatment of the rind comprises:
    removing an outer skin of the rind, and grounding the rind into a powder after being dried; subjecting the powder to an ultrasound-enzyme assisted solvent leaching and filtering to obtain a filter residue and a primary extraction solution; subjecting the filter residue to the ultrasound-enzyme assisted solvent leaching, and then filtering to obtain a secondary extraction solution; and mixing the secondary extraction solution with the primary extraction solution and a pulp supernatant which is obtained by centrifuging the pulp to obtain a pretreatment material for extracting Citrulline.

8. The method for simultaneously extracting Lycopene and Citrulline from the watermelon according to claim 6, wherein the ultrasonic-enzyme-assisted solvent leaching comprises:

adding water to the filtered residue at a material-liquid ratio of 1:10-1:20 (kg/L), and then adding 0.1% (m/m) of pectinase and 0.1% (m/m) of cellulose to the filtered residue and water; adjusting pH to 4.0, ultrasonic power to 100-140 W, extraction temperature to 30-50° C., extraction time to 60-120 min, and extraction times to twice.

9. The method for simultaneously extracting Lycopene and Citrulline from the watermelon according to claim 6, wherein extracting Citrulline comprises:

(1) microbial fermentation: adding 5% (v/v) yeast to the supernatant to ferment for 24 h to remove sugar;

(2) ion-exchange resin purification: filtering the supernatant after microbial fermentation to remove yeasts, and adding to an activated wet resin to adsorb Citrulline, and then eluting with 0.5 mol/L ammonia solution at an elution rate of 2 BV/h to obtain a Citrulline eluent;

(3) macroporous adsorption resin discoloration: mixing an activated wet resin with the Citrulline eluent at 1:20 (g/mL), and performing a static adsorption on condition of 100-150 r/min for 2 h at room temperature to obtain a crude Citrulline extract;

(4) crystallization and recrystallization:

a. concentrating the crude Citrulline extract under vacuum to a soluble solid content of ≥30%, adjusting the pH of the concentrated solution to 5.97, and precipitating Citrulline crystals at 4° C.; centrifuging, washing, and drying to obtain a white powdered solid of Citrulline crystals;

b. dissolving the white powdered solid of step (a) in water, adjusting the pH to 5.97, adding 0.1% Citrulline crystals as seed crystals, precipitating the Citrulline crystals at 4° C., and centrifuging to separate the Citrulline crystals;

c. repeating the step (b) 1-2 times to obtain a refined solid powder of Citrulline.

\* \* \* \* \*